(12) United States Patent
Dupuis et al.

(10) Patent No.: US 7,452,662 B2
(45) Date of Patent: Nov. 18, 2008

(54) METHOD OF EXPANDING AND DIFFERENTIATING CORD BLOOD CELLS BY HYPERTHERMIC INCUBATION

(75) Inventors: Nicolas Dupuis, Québec (CA); Chantal Proulx, Sainte-Foy (CA)

(73) Assignee: Hema-Quebec, Saint-Laurent (CA)

( * ) Notice: Subject to any disclaimer, the term of this patent is extended or adjusted under 35 U.S.C. 154(b) by 236 days.

(21) Appl. No.: 11/113,074

(22) Filed: Apr. 25, 2005

(65) Prior Publication Data

US 2005/0266557 A1    Dec. 1, 2005

Related U.S. Application Data

(60) Provisional application No. 60/564,581, filed on Apr. 23, 2004.

(51) Int. Cl.
    *A01N 1/02* (2006.01)
(52) U.S. Cl. ......................................................... 435/2
(58) Field of Classification Search ....................... None
    See application file for complete search history.

(56) References Cited

FOREIGN PATENT DOCUMENTS

WO    WO-00/28813 A1    5/2000
WO    WO-02/100898 A2   12/2002

OTHER PUBLICATIONS

Ashman et al., "Effect of incubation temperature on mitogen responses of lymphocytes from adult peripheral blood and from cord blood", Clin. Exp. Immunol. 33 : 319-326 (1978).*
Barnes et al., Cell Stress & Chaperones, No. 6, vol. 4, pp. 316-325, 2001.
Bruno et al., Haematologica, vol. 88, No. 4, pp. 379-387, 2003.
de Benedetti et al., The Journal of Biological Chemistry, vol. 261, No. 33, pp. 15800-15804, 1986.
Ferris et al., Natl. Acad. Sci. USA, vol. 85, pp. 3850-3854, 1988.
Gidáli et al., Stem Cells, vol. 18, No. 3, pp. 533-538, 1994.
Kanamaru et al., Stem Cells, vol. 18, No. 3, pp. 190-195, 2000.
Katschinski et al., Cancer Letters, No. 115, pp. 195-199, 1997.
Katschinski et al., Cytokine and Growth Factor Reviews, No. 10, pp. 93-97, 1999.
Kie et al., Stem Cells, No. 20, pp. 73-79, 2002.
Kim et al., Mol. Cells, vol. 14, No. 3, pp. 367-373, 2002.
Larocca et al., Int. J. Cancer, No. 73, pp. 75-83, 1997.
Milarski et al., Proc. Natl. Acad. Sci. USA, vol. 83, pp. 9517-9521, 1986.
Ménoret et al., International Journal of Hyperthermia, vol. 18, No. 6, pp. 490-505, 2002.
Pick et al., Exp. Hematol., vol. 30, No. 9, pp. 1079-1087, 2000.
Proulx et al., Journal of Hematotherapy & Stem Cell Research, No. 12, pp. 179-188, 2003.
Proulx et al., Biotechnol Bioeng., vol. 88, No. 6, p. 675-680, 2004.
Robins et al., Cancer Research, No. 48, pp. 6587-6592, 1988.
Robins et al., Journal of Clinical Oncology, vol. 11, No. 9, pp. 1787-1794, 1993.
Robins et al., Journal of Clinical Oncology, vol. 15, No. 1, pp. 158-164, 1997.
Robins et al., Cancer Letters, No. 97, pp. 195-201, 1995.
Sigurjónsson et al., Journal of Hematotherapy & Stem Cell Research, No. 11, pp. 389-400, 2002.
Su et al., Marrow Transplantation, No. 27, pp. 1075-1080, 2001.
Wierenga et al., Experimental Hematology, No. 31, pp. 421-427, 2003.
Kluger, M.J., et al., Annals New York Academy of Sciences, vol. 856, pp. 224-233, 1998.
Ashman, R.B., et al., Effect of incubation temperature on mitogen responses of lymphocytes from adult peripheral blood and from cord blood, Clin. exp. Immunol., vol. 33, pp. 319-326, (1978).
Shen, Rong-Nian et al., Influence of elevated temperature on natural killer cell activity, lymphokine-activated killer cell activity and lectin-dependent cytotoxicity of human umbilical cord blood and adult blood cells, International Journal of Radiation Oncology Biology Physics, vol. 29, No. 4, pp. 821-826, Database Biosis [Online], Biosciences Information Service, Philadelphia, PA, US; 1994, XP00246605.
Boucher, Jean-Francois et al., Identification of the mechanisms responsible for the increased megakaryopoiesis at 39 degrees C., vol. 108, No. 11, Part 1, Database Biosis [Online] , Biosciences Information Services, Nov. 2006, XP002466506.
Podesta, Marina et al., Modified in vitro conditions for cord blood-derived long-term culture-initiating cells, Experimental Hematology, vol. 29, pp. 309-314, 2001.

* cited by examiner

*Primary Examiner*—Sandra E. Saucier
(74) *Attorney, Agent, or Firm*—Birch, Stewart, Kolasch & Birch, LLP

(57) ABSTRACT

Based on previous evidence suggesting positive effects of fever on in vivo hematopoiesis, the effect of hyperthermia on the expansion and differentiation of megakaryocytes (MKs) in ex vivo cultures of CB CD34-enriched cells has now been tested. Cells were cultured at 37° C. or 39° C. for 14 days in cytokine conditions optimized for MK development, and analyzed periodically by microscopy, flow cytometry and colony assays. Compared to 37° C., cultures maintained at 39° C. produced much more total cells (5×), MK progenitors (9×) and total MKs (7×), and showed accelerated (3-4 days) and enhanced MK maturation with increased yields of proplatelets and platelets (11.7×). The increased number of CD34+ cells and myeloid progenitors in the 39° C. cultures also suggested a general stimulatory effect of hyperthermia on the expansion of more primitive stem/progenitor cells and of cells of other lineages.

6 Claims, 8 Drawing Sheets

39°C

METHOD OF EXPANDING AND DIFFERENTIATING CORD BLOOD CELLS BY HYPERTHERMIC INCUBATION

This Nonprovisional application claims priority under 35 § U.S.C. 119(e) on U.S. Provisional Application No. 60/564,581 filed on Apr. 23, 2004, the entire contents of which are hereby incorporated by reference.

TECHNICAL FIELD

The present invention relates to a new method of expanding cord blood cells such as megakaryocytes.

BACKGROUND OF THE INVENTION

The identification of thrombopoietin (TPO) has allowed the generation of megakaryocytes (MK) and platelets in ex vivo cultures. TPO and various cytokines have been shown to act in synergism for optimal MK viability and yield (Sigurjonsson OE, et al., *J Hematother Stem Cell Res.* 11:389-400, 2002; Williams J L, et al., *Blood* 91:4118-4126, 1998; Su R J, et al., *Bone Marrow Transplant* 27:1075-1080, 2001; and Kie J H, et al., *Stem Cells* 20:73-79, 2002). It has recently been reported that early and late variations of cytokine concentrations could promote the in vitro TPO-dependent generation of MKs from cord blood (CB) CD34-enriched cells (Proulx C, et al., *J Hematother Stem Cell Res.* 12:179-188, 2003). It is expected that other biochemical and/or biophysical factors could further enhance MK yield. Whole body hyperthermia in combination with chemo- or radiotherapy has been used for several years in the treatment of cancers. Animal and clinical data showed that transient body hyperthermia had several beneficial effects including more efficient bone marrow engraftment and protection against therapy-induced thrombocytopenia (Robins H I, et al. *Cancer Res.* 48:6587-6592, 1988; Robins H I, et al., *J Clin Oncol.* 11:1787-1794, 1993; Woods J P, et al., *Can J Vet Res.* 60:75-78, 1996; Robins H I, et al., *J Clin Oncol.* 15:158-164, 1997; Katschinski D M, et al., *Cancer Lett.* 115:195-199, 1997; and Katschinski D M, et al., *Cytokine Growth Factor Rev.* 10:93-97, 1999). These effects have been associated with rapid (60 minutes) increases of several cytokines in the plasma and bone marrow of hyperthermia-treated patients (Robins H I, et al., *Cancer Lett.* 97:195-201, 1995). Although these cytokines could have stimulatory effects, one cannot rule out a direct possible effect of hyperthermia on stem/progenitor cells.

It would be highly desirable to be provided with a new method for culturing MKs allowing to obtain better yield of cells than existing methods, thus further allowing a better platelet production than existing culture methods.

SUMMARY OF THE INVENTION

One aim of the present invention is to provide a new method for culturing MKs allowing to obtain better yield of cells than existing methods, thus further allowing a better platelet production than existing culture methods. To achieve this aim, the inventors sought to determine the effect of elevated temperature by comparing the yields of MKs and platelets obtained in cultures maintained above 37° C. (such as at 39° C.) versus 37° C.

In accordance with the present invention there is provided a new method for culturing megakaryocytes, cord blood cells or CD34-enriched cells.

In accordance with the present invention, there is provided a method for culturing cord blood cells, comprising the step of incubating said cord blood cells in a suitable medium, under suitable conditions and for a time sufficient for multiplication of cells at a temperature between 37° C. and 41° C., and preferably at a temperature of 38° C. to 40° C., and more preferably at a temperature of 39° C.

In the present application, the term "suitable medium" is meant to include any culture medium that would permit culturing cord blood cells. Such media are well known in the art and many are commercially available.

In the present application, the term "suitable conditions" is meant to include every conditions but temperature required to expand cord blood cells, the temperature being a distinct condition. Accordingly, suitable conditions include for example, without limitations, conditions of humidity, $CO_2$ content and $O_2$ content in the gaseous environment contacting the medium of culture.

In the present application, the terms "culture" and "culturing" are interchangeably used with or for "expand" and "expansion", respectively. In the context of the present application, culturing cord blood cells and expanding same is meant to mean the same thing.

BRIEF DESCRIPTION OF THE DRAWINGS

(FIG. 5A) and 39° C. (FIG. 5B), illustrating the effect of heat treatment on CB CD34-enriched cells in ex vivo cultures;

DETAILED DESCRIPTION OF THE PREFERRED EMBODIMENT

In accordance with the present invention, there is provided a new method of culturing megakaryocyes under standard conditions but for the temperature at which the culture is maintained or made. The temperature in accordance with the present invention is preferably set to 39° C. instead of 37° C. as is currently being done in the art. However, it is clear from the data and figures reported herein that a temperature above 37° C. and below 41° C. is beneficial to the culture. Accordingly, it is intended to cover a temperature range varying from (but excluding) 37° C. to less than 41° C., and preferably from 38° C. to 40° C. Although one skilled person in the art will appreciate that a temperature of 41° C. is not useful in accordance with the present invention, the skilled person will be apt without difficulty and undue experiments to determine a temperature below 41° C. at which culture can still be made (with the same benefit) as in the present invention. It is thus not the intention to seek protection at a temperature covered by the prior art (37° C.), nor at a temperature at which cells cannot be cultured. It was surprisingly discovered that a temperature above the normal condition of culture, i.e. above 37° C., was beneficial to the culture, allowing to obtain a better yield of cells (larger expansion).

Figure 1:
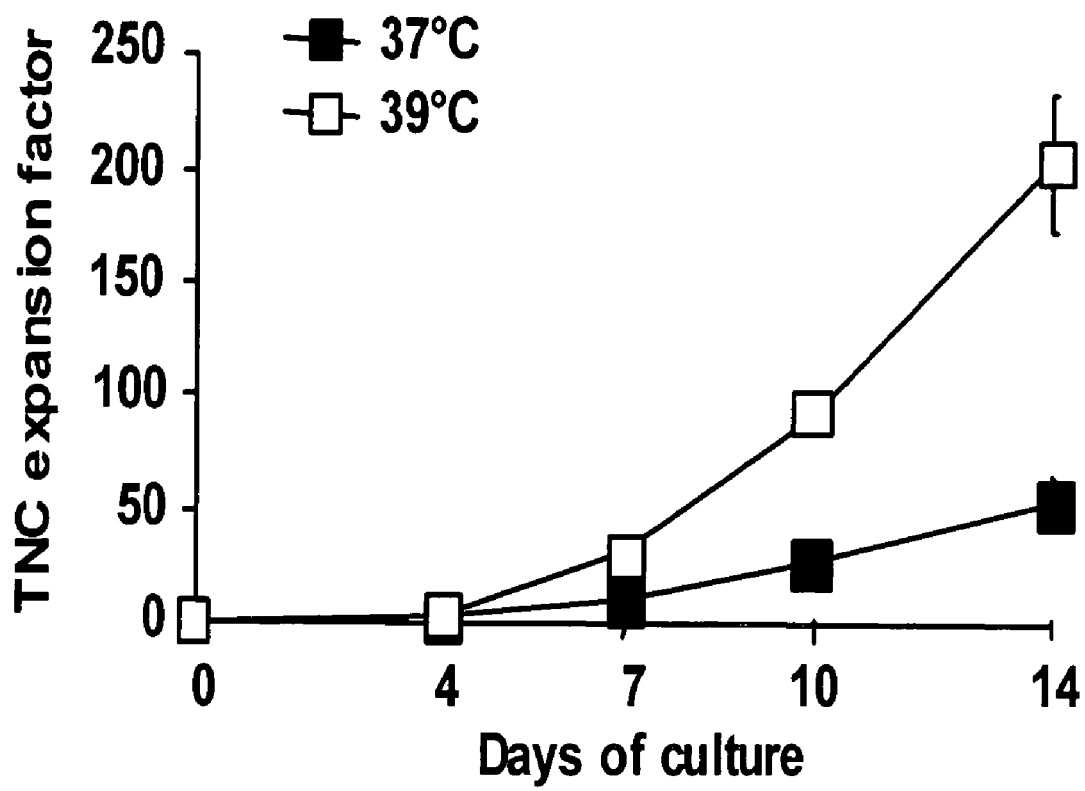
FIG. 1 illustrates the effect of heat treatment of CB CD34-enriched cells on the total nucleated cell (TNC) expansion factor in ex vivo cultures.
Figure 2:
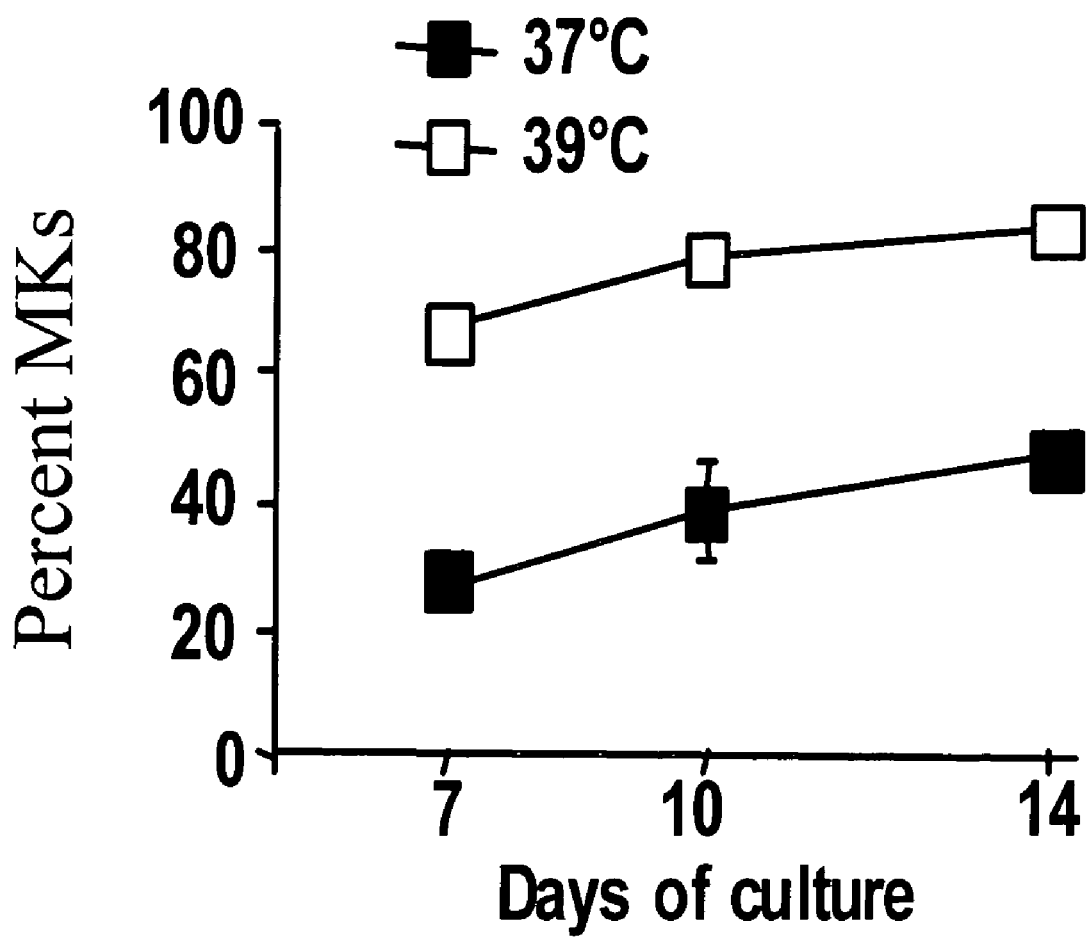
FIG. 2 illustrates the effect of heat treatment of CB CD34-enriched cells on the percentage of total MKs per culture after expansion in ex vivo cultures.

The inventors have recently reported that preferential MK expansion could be achieved by culturing CB CD34-enriched cells in medium containing TPO and interleukin-6 and low amounts of stem-cell-factor and Flt3-ligand to promote expansion and differentiation of MK-committed cells (Proulx C, et al., *J Hematother Stem Cell Res.* 12:179-188, 2003, the entire content of which is hereby incorporated by reference). These culture conditions were thus used to determine the effect of temperature (from 37° C. to 41° C., and more particularly between 39° C. versus 37° C.) in culture. In experiments, it was observed that the continuous culture at 38° C., 39° C. or 40° C. did not result in reduced viability of the cells. Comparative experiments each starting from the same population of CD34-enriched cells, showed a significant increase in the expansion of total nucleated cells (TNC) in cultures maintained at 39° C. compared to 37° C. (FIG. 1): 2.7-, 3.5- and 4.9-fold at days 7, 10, and 14, respectively (p=0.01). In FIG. 1, total nucleated cell (TNC) counts were determined by Trypan blue exclusion and expressed as the number of expanded TNC per day-0 seeded cell. Flow cytometry analysis of expanded cells for MK markers further showed a significant increase in proportions of CD41a+ MK cells in cultures expanded at 39° C. (FIG. 2, 2- to 2.5-fold versus cultures at 37° C.), thus indicating the generation of seven times (7×) more total MKs per seeded cell at 39° C. (168.6 ±28 versus 24.8 ±4 total MKs at 39° C. versus 37° C.). In FIG. 2, total MK frequency was determined by flow cytometry as the percentage of TNC expressing the CD41a surface marker.

To determine the optimal temperature above 37° C., cultures were also done at 38° C., 40° C. and 41° C. in addition to 39° C. The results (FIG. 3) showed that the maximal stimulatory effect of the temperature on the expansion of total cells and megakaryocytes was obtained at 39° C. Stimulatory effects were also observed at 38° C. and 40° C. but were less important than the one at 39° C. No viable cells were observed in cultures maintained at 41° C.

Figure 4:
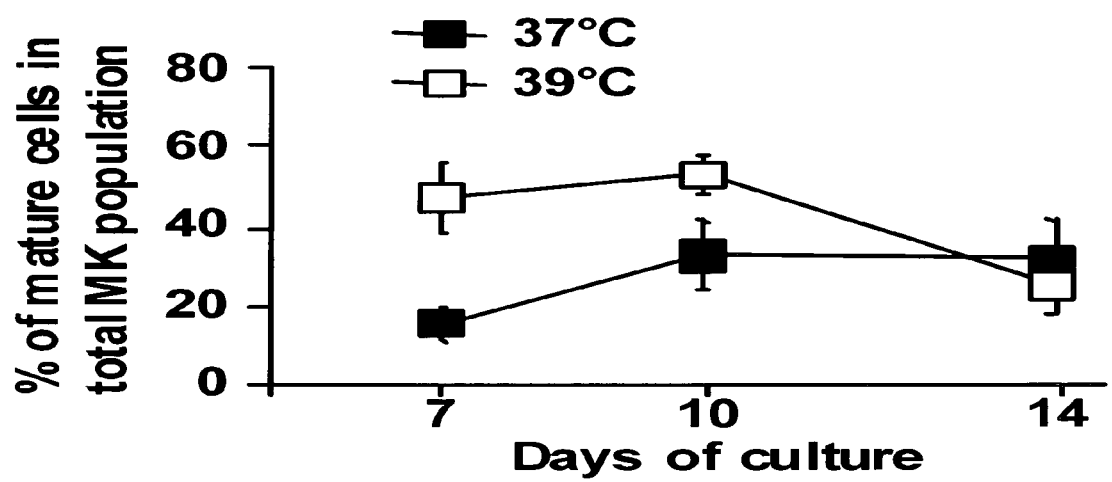
FIG. 4 illustrates the effect of heat treatment of CB CD34-enriched cells on the percentage of mature cells in the total MK population of expanded cells in ex vivo cultures.
Figure 5A:
FIGS. 5A and 5B are photomicrographs of Hoffmann modulation contrast images of day-7 expanded cells at 37° C.
Figure 5B:
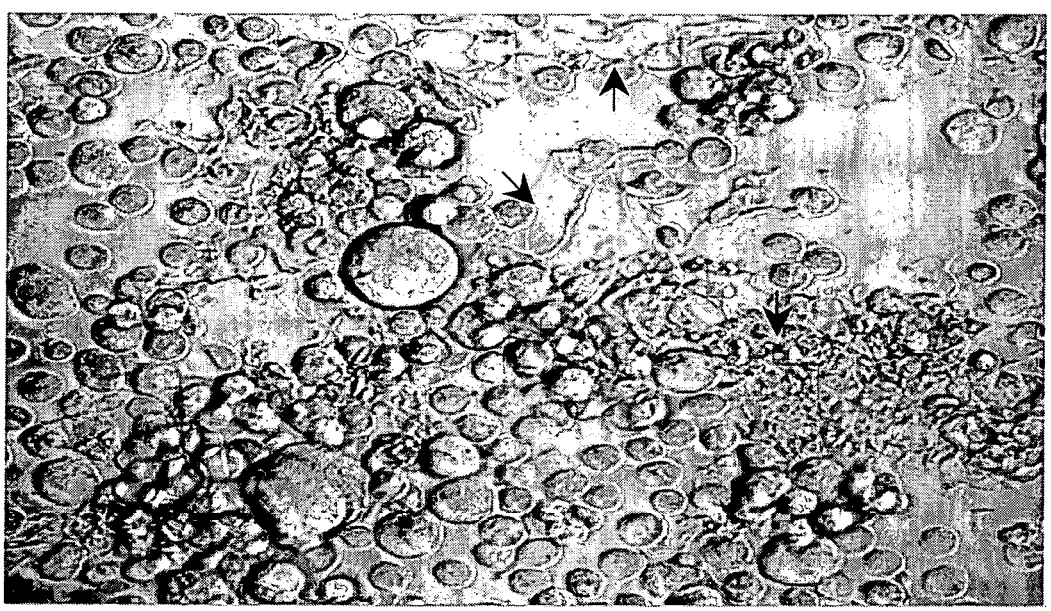
Figure 6:
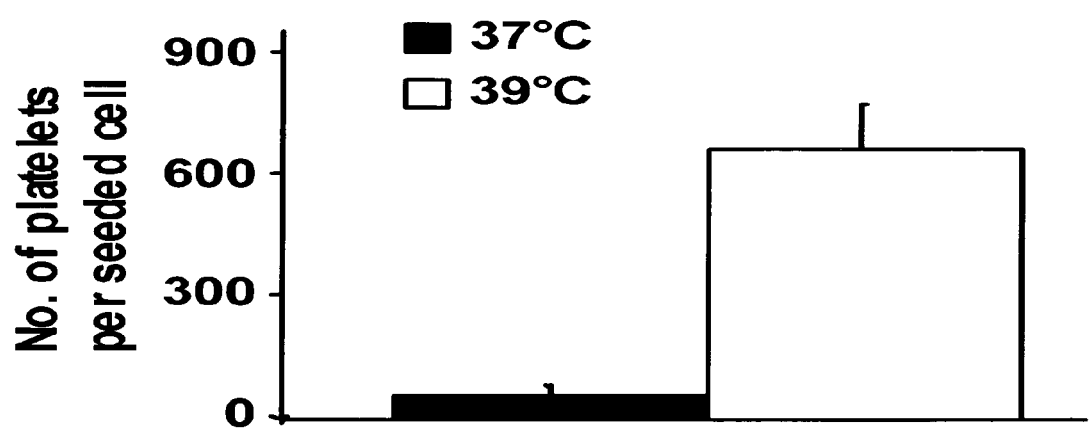
FIG. 6 illustrates the effect of heat treatment of CB CD34-enriched cells on the number of platelets per seeded cell after expansion in ex vivo cultures.

Moreover, MK maturation as determined by the expression of the late CD42b marker by flow cytometry and the presence of MK-displaying proplatelets by microscopy, was observed earlier (by 3 to 4 days) and in higher proportions in 39° C. cultures (FIG. 4, 3- and 1.6-fold more total CD41a+ MKs expressed CD42b at days 7 and 10; FIGS. 5A and 5B, proplatelets observed at day 7 in cultures at 39° C., (FIG. 5B) versus none at 37° C., (FIG. 5A)). In FIG. 4, mature MK frequency was determined by flow cytometry as the percentage of total CD41a+ MKs expressing the CD42b surface marker. In FIG. 5B, arrowheads indicate proplatelet extensions. In FIGS. 5A and 5B, original magnification ×400. As expected from the increased MK maturation, platelet production in day-14 cultures at 39° C. was 11.7-fold higher compared to 37° C. (FIG. 6). In FIG. 6, absolute numbers of platelets at day 14 were determined by flow cytometry as CD41a+ events with the same scatter properties as blood platelets.

Figure 7:
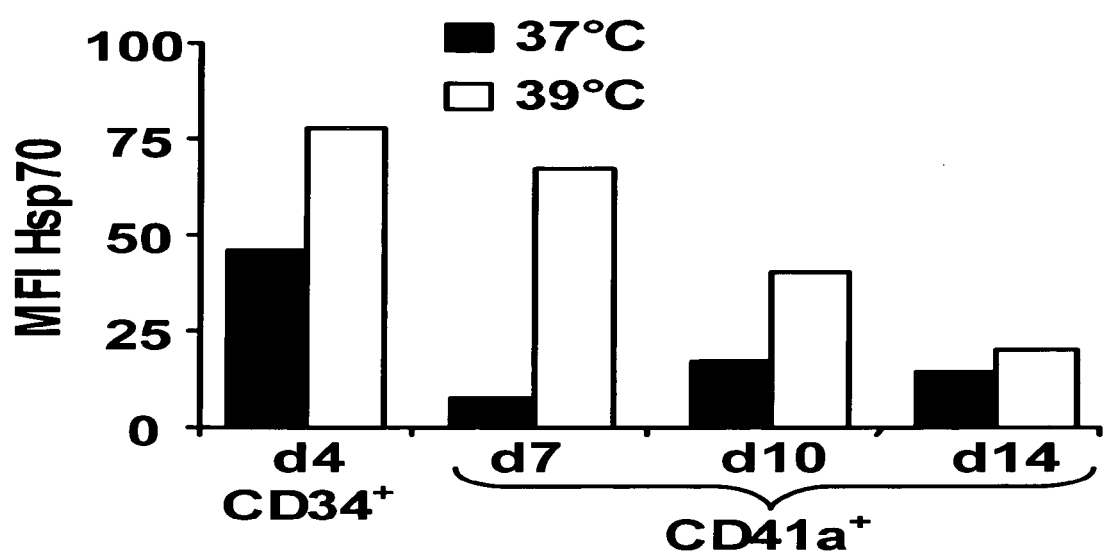
FIG. 7 illustrates the effect of heat treatment of CB CD34-enriched cells on intracellular expression of the inducible Hsp70 after expansion in ex vivo cultures.

A well-known effect of hyperthermia on mammalian cells is the induction of expression of genes coding for heat shock proteins. Given the important role of the highly heat-inducible Hsp70 in cell protection, growth, development and activity (Barnes J A, et al., *Cell Stress Chaperones.* 6:316-325, 2001; Milarski K L, et al., *Proc Natl Acad Sci USA.* 83:9517-9521, 1986; de Benedetti A, Baglioni C. *J Biol. Chem.* 261: 15800-15804, 1986; Ferris D K, et al., *Proc Natl Acad Sci USA.* 85:3850-3854, 1988; Zakeri Z F, Wolgemuth D J. *Mol Cell Biol.* 7:1791-1796, 1987; and Ménoret A, et al., *Int J Hyperthermia* 18:490-505, 2002), its expression in specific cells at different times (FIG. 7) was investigated. Day-7 and -10 CD41a+ MKs cultured at 39° C. had respectively a 8- and 2-fold higher Hsp70 content compared to MKs maintained at 37° C. In FIG. 7, intracellular expression of the inducible Hsp70 was analyzed by flow cytometry in day-4 CD34+ cells or day-7, -10 and -14 total CD41a+ MKs. Similarly, CD34+ cells expanded for 4 days at 39° C. contained significantly more Hsp70 protein than those at 37° C. indicating a stimulatory effect of 39° C. culture on the expansion of more primitive stem/progenitor cells as well. This is supported by the observation that the early 39° C. culture of the CD34-enriched cells was required to maximize the MK yield in the late phase. This possibility was tested using colony assays to determine the clonogenic potential of MK and total myeloid progenitors under these conditions. Nine times (9×) more CFC-MK were obtained in cultures maintained at 39° C. for 14 days compared to cultures at 37° C. (Table 1).

TABLE 1

Expansion of MK and total myeloid progenitors

| | Expansion of CFCs* vs. day 0 (% of total expanded cells) | | |
|---|---|---|---|
| | Day 7 | Day 10 | Day 14 |
| CFC-MK† | | | |
| 37° C. | 11.2 (3.4%) | 21.4 (2.7%) | 5.7 (0.4%) |
| 39° C. | 14.3 (1.6%) | 82.6 (2.0%) | 48.9 (0.7%) |
| CFC-TOT‡ | | | |
| 37° C. | 5.9 (11.6%) | 10.7 (8.8%) | 10.9 (4.5%) |
| 39° C. | 8.7 (6.4%) | 22.8 (3.6%) | 20.3 (2.0%) |

*Expansion of CFCs: TNC expansion factor × % of CFCs at each day of culture divided by % of CFCs at day 0
†Mean frequency of CFC-MK at day 0: 2.3%
‡Mean frequency of CFC-TOT at day 0: 15%
CFC-MK indicates MK colony-forming cells;
CFC-TOT, total myeloid colony-forming cells A significant increase in CFC-TOT was also observed (2-fold). This lower increase may be due to the use of cytokine conditions that were optimized for MK development. A stimulatory effect of 39° C. culture on hematopoietic stem cells would facilitate procedures such as transplantation and gene therapy where the low number of cells (e.g. CB stem cells) limits clinical interventions.

The extensive previous work on hyperthermia has shown that transformed cells were more sensitive to killing by a short heat treatment in combination with cytotoxic chemicals, than normal cells (Gidali J, et al., *Stem Cells* 12:533-538, 1994; Larocca L M, et al., *Int J Cancer* 73:75-83, 1997; and Wierenga P K, et al., *Exp Hematol.* 31:421-427, 2003). Control experiments conducted in accordance with the present invention showed that the viability of several transformed cell lines was unaffected or decreased by continuous culture at 39° C. The unexpected finding that normal hematopoietic cells grow more efficiently at 39° C. indicate that cell culture at 37° C. is a paradigm that needs to be reassessed at least for the various types of normal cells that are cultured ex vivo.

Materials and Methods

Figure 3:
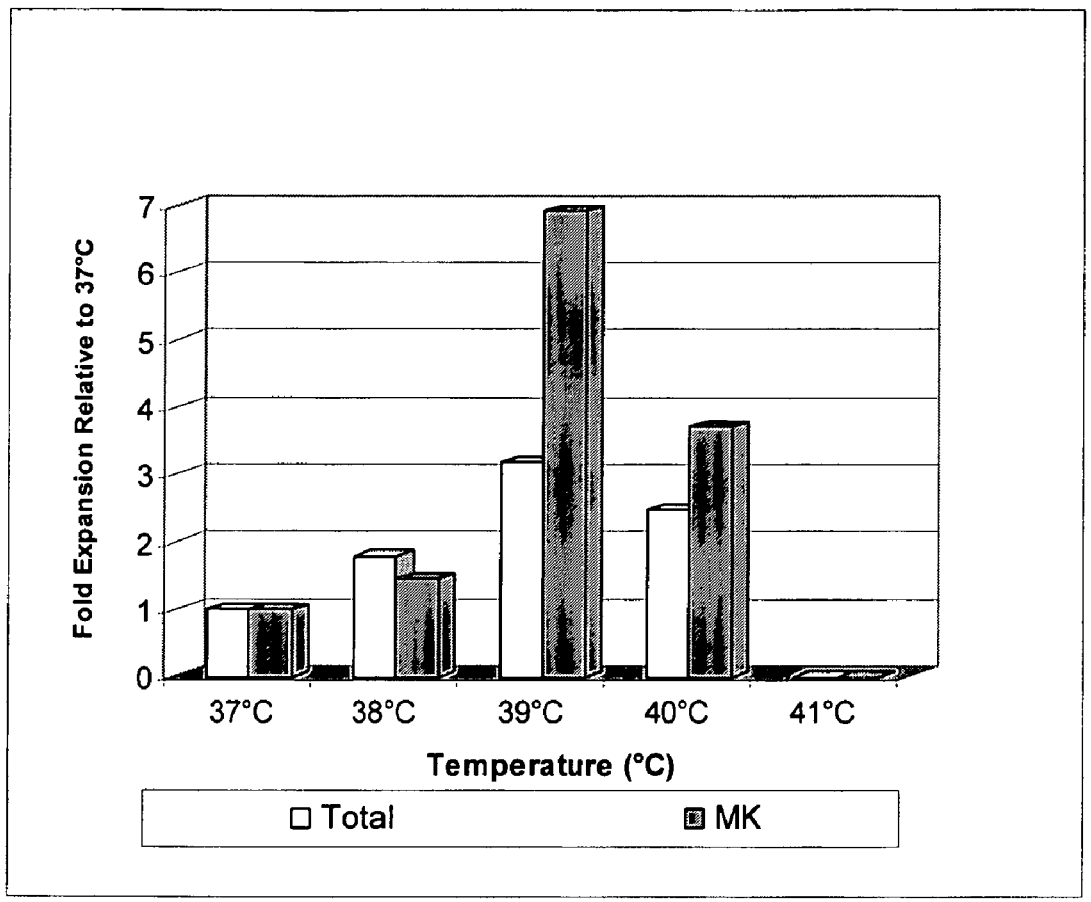
FIG. 3 illustrates the effect of heat treatment from 37° C. to 41° C. on CB CD34-enriched cells in ex vivo cultures.

Having determined in FIG. 3 that the optimal temperature was 39° C., all subsequent experiments were made at 39° C., where a maximal response was seen. This should not be construed even implicitly that other temperatures, such as 38° or 40° C., are to be excluded from the present invention.

Accordingly, in FIGS. 1 to 7, twenty thousand cells per mL of culture were incubated at 37° C. or 39° C. for 14 days. Cell analysis was performed at specific time points in each culture corresponding to medium and/or cell concentration adjustments.

In Vitro Culture of MKs from CB CD34-enriched Cells

Collection of human umbilical CB samples from healthy full-term neonates with informed consent of mothers, preparation and culture of CD34-enriched cells were done as described in Proulx et al. (Proulx C, et al., supra). Cells were cultured with the following recombinant human cytokines (R&D Systems, Minneapolis, Minn., USA): TPO (100 ng/mL), stem-cell-factor (2.5 ng/mL), Flt3-ligand (2.5 ng/mL) and interleukin-6 (50 ng/mL). Cultures were maintained at 37° C. or 39° C. for 14 days under fully humidified conditions in an atmosphere of 20% $O_2$ (air) and 10% $CO_2$. Temperature in the incubator chambers was validated with the NIST traceable thermometer.

Flow Cytometry Analysis

Freshly selected CB CD34-enriched cells or cells expanded for various time intervals were phenotyped by flow cytometry using a FACS-Calibur™ flow cytometer (Becton Dickinson Immunocytometry Systems, San Jose, Calif.) as reported in Proulx et al. (Proulx et al., supra). Mouse IgG1 monoclonal antibodies used in the assays were: anti-human CD34-phycoerythrin-conjugated, anti-human CD42b-fluorescein isothiocyanate (FITC) (both antibodies were purchased from Immunotech, Beckman Coulter Co., Marseille, France), anti-human CD41a-allophycocyanin-conjugated (Beckton Dickinson) and anti-heat shock protein 70 (Hsp70)-unlabeled (Stressgen Biotechnologies, Victoria, BC, Canada). The anti-Hsp70 antibody was labeled with the Fluo-Reporter FITC Protein Labeling kit (Molecular Probes, Inc., Eugene, Oreg.) prior to use. Intracellular staining of Hsp70 was performed by incubating washed cells with the anti-Hsp70-FITC antibody in a permeabilization solution containing 0.1% Triton X-100™ (Bio-Rad Laboratories, Life Science Research, Hercules, Calif., USA). Quantitation of specific Hsp70 expression was determined by subtracting the mean fluorescence intensity of the isotype control cells from the one of the anti-Hsp70-labeled cells.

Progenitor Assays

MK colony assays were performed using the MegaCult™-C collagen-based system (StemCell Technologies, Vancouver, BC, Canada), according to the manufacturer's instructions, and as described in Proulx et al. (Proulx et al., supra). Assays for quantitation of human clonogenic hematopoietic progenitor cells were performed using the MethoCult™SF$^{BIT}$H4436 (StemCell Technologies), according to the manufacturer's instructions. Components for this medium were selected to support optimal growth of human erythroid, granulocyte-macrophage and multilineage colonies (total myeloid colonies, CFC-TOT). CFC-TOT in each culture were scored after 14 days.

Statistical Analysis

Results were expressed as means (±SEM) of data obtained from three independent experiments. Significance levels were determined using Student's t-test.

The references cited therein are all hereby incorporated by reference in their entirety.

While the invention has been described in connection with specific embodiments thereof, it will be understood that it is capable of further modifications, and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

What is claimed is:

1. A method for increasing the rate of proliferation of nucleated cells in a CD34$^+$ enriched cord blood cell composition comprising:

incubating the CD34$^+$ enriched cord blood cell composition in a suitable medium comprising thrombopoietin, interleukin-6, stem-cell factor and fms-like tyrosine kinase-3 ligand, under suitable conditions and for a time sufficient for multiplication of nucleated cells at a temperature of more than 370° C. and less than 41° C.

2. The method of claim 1, wherein said temperature is from 38° C. to 40° C.

3. The method of claim 2, wherein the temperature is 39° C.

4. A method for culturing cord blood enriched in CD34$^+$ cells to enrich the culture for megakaryocytes, myeloid progenitors and platelets comprising:

incubating the CD34$^+$ enriched cord blood cells in a suitable medium comprising thrombopoietin, interleukin-6, stem-cell factor and fms-like tyrosine kinase3 ligand, under suitable conditions and for a time sufficient for multiplication of CD34$^+$ cells at a temperature of more than 37° C. and less than 41° C.

5. The method of claim 4 wherein the culture is maintained for a period of from 7 to 10 days.

6. The method of claim 4, wherein the temperature is 39° C.

* * * * *